(12) United States Patent
Papin et al.

(10) Patent No.: US 8,753,824 B2
(45) Date of Patent: Jun. 17, 2014

(54) SERIAL MULTIPLE ANTIGEN COLOCALIZATION IN PARAFFIN-EMBEDDED TISSUE

(75) Inventors: Jason A. Papin, Charlottesville, VA (US); James W. Mandell, Charlottesville, VA (US); George F. Glass, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 78 days.

(21) Appl. No.: 13/262,282

(22) PCT Filed: Apr. 2, 2010

(86) PCT No.: PCT/US2010/029763
§ 371 (c)(1),
(2), (4) Date: Oct. 5, 2011

(87) PCT Pub. No.: WO2010/115089
PCT Pub. Date: Oct. 7, 2010

(65) Prior Publication Data
US 2012/0021439 A1    Jan. 26, 2012

Related U.S. Application Data

(60) Provisional application No. 61/166,384, filed on Apr. 3, 2009.

(51) Int. Cl.
*G01N 33/53* (2006.01)
*G01N 33/58* (2006.01)
*G01N 33/50* (2006.01)

(52) U.S. Cl.
CPC .......... *G01N 33/5023* (2013.01); *G01N 33/581* (2013.01); *G01N 2800/60* (2013.01)
USPC ............................................. 435/7.1; 435/7.2

(58) Field of Classification Search
None
See application file for complete search history.

(56) References Cited

U.S. PATENT DOCUMENTS

| | | | |
|---|---|---|---|
| 8,168,169 B2 * | 5/2012 | Cataldo et al. | 424/93.21 |
| 2006/0188140 A1 * | 8/2006 | Gholap et al. | 382/133 |
| 2008/0273788 A1 * | 11/2008 | Soenksen et al. | 382/133 |

OTHER PUBLICATIONS

Shi et al. (J. Histochem & Cytochem 1995, vol. 43, p. 193-201).*
Beltrame et al. (SPIE 1995, vol. 2412, p. 222-229).*
Lan et al. (J. Histochemistry and Cytochemistry 1995 vol. 43, p. 97-102).*
Li et al. (Histochem Cell Biol. 2014 vol. 141, p. 251-262).*
Anthony, et al., "B lymphocytes in the normal brain: contrasts with HIV-associated lymphoid infiltrates and lymphomas", Brain, 2003, vol. 126, pp. 1058-1067, May 31, 2003.
Tramu, et al., "An efficient method of antibody elution for the successive or simultaneous localization of two antigens by immunocytochemistry", The Journal of Histochemistry and Cytochemistry, 1978, vol. 26, No. 4, pp. 322-324, Apr. 30, 1978.
Scopsi and Larson, "Bodian's silver impregnation of endocrine cells. A tentative explanation to the staining mechanism", Histochemistry, 1986, vol. 86, No. 1, pp. 59-62, Jan. 31, 1986.
Glass, et al., "SIMPLE: a sequential immunoperoxidase labeling and erasing method", Journal of Histochemistry & Cytochemistry, 2009, vol. 57, No. 10, pp. 899-905, Apr. 13, 2009.
Pirici, et al., "Antibody Elution Method for Multiple Immunohistochemistry on Primary Antibodies Raised in the Same Species and of the Same Subtype", Journal of Histochemistry & Cytochemistry, vol. 57(6): pp. 567-575, 2009.
Caruccio, et al., "A novel method using formamide for the elution of anbibodies from erythrocytes", 2002 Blackwell Science Ltd., Vox Sanguinis (2002) 83, 63-69.
Robertson, et al., "Multiple immunofluorescence labeling of formalin-fixed paraffin-embedded (FFPE) tissue", BMC Cell Biology 2008, 9:13, http://www.biomedcentral.com/1471-2121/9/13.

* cited by examiner

*Primary Examiner* — Jacob Cheu
(74) *Attorney, Agent, or Firm* — Rodney L. Sparks

(57) ABSTRACT

The present invention provides a novel method called Sequential IMmunoPeroxidase Labeling and Erasing (SIMPLE) that enables the simultaneous visualization of at least five markers within a single tissue section. Utilizing the alcohol-soluble peroxidase substrate 3-amino-9-ethylcarbazole (AEC), combined with a rapid non-destructive method for antibody-antigen dissociation, the present application discloses the ability to erase the results of a single immunohistochemical stain while preserving tissue antigenicity for repeated rounds of labeling. The present invention also provides methods for visualizing multiple antigens simultaneously.

36 Claims, 4 Drawing Sheets

SERIAL MULTIPLE ANTIGEN COLOCALIZATION IN PARAFFIN-EMBEDDED TISSUE

CROSS REFERENCE TO RELATED APPLICATIONS

This application is a national stage filing of International Application No. PCT/US2010/029763, filed Apr. 2, 2010, which is entitled to priority pursuant to 35 U.S.C. §119(e) to U.S. provisional patent application No. 61/166,384, filed on Apr. 3, 2009. The entire disclosures of the afore-mentioned patent application are incorporated herein by reference.

BACKGROUND

Visual colocalization of molecular species within sectioned tissue can provide insights into cellular biochemistry and can serve as the basis for further study of protein-organelle and protein-protein interactions. Visualization of abnormal protein coexpression in neoplastic tissue may elucidate components of oncogenic signaling pathways. Colocalization of COX2 and laminin-5, for example, has been observed at the cancer-stromal interface of lung adenocarcinoma and may be associated with abnormalities in p53 expression (1). Additionally, colocalization of β-catenin with compartment-specific markers revealed prognostic significance that was not found using traditional single stain methods (2).

Current colocalization methods, however, have several limitations. The most commonly used method, multi-color immunofluorescence (MCIF), is limited by the number of viable combinations of available fluorescent tags and can be negatively affected by spectral bleed-through, antibody cross-reactivity, photo-bleaching, and autofluorescence of paraffin-embedded tissue (3). Because of these limitations, this method is usually restricted to the simultaneous visualization of just two antigens plus a nuclear counterstain. Peroxidase or alkaline phosphatase-linked multicolor immunostaining is possible, but the maximum number of chromogenic substrates that can be differentiated within a single section is typically two or three (4). Moreover, multiple chromogenic substrates do not allow colocalization in the same cellular compartment due to the obscuring of lighter colors by darker chromogens. Additionally, the use of more than one primary antibody from the same species (i.e., mouse or rabbit) is usually impossible due to secondary antibody cross-reactivity.

A recent report of a multiplex immunostaining chip demonstrated simultaneous staining of a large section with a grid of many different antibodies, but since different portions of the tissue section are stained with each probe no colocalization information is obtained (5).

There is a long felt need in the art for compositions and method useful for detecting and visualizing multiple antigens in a sample such as a cell or tissue sample. The present invention satisfies these needs.

SUMMARY OF THE INVENTION

The present invention provides novel methods for visualization of multiple different antigens in cell and tissue samples. More specifically, the present application discloses methods for sequential labeling of cells and tissues, because methods have been developed to successfully remove a label once detected, and to add a new label. In one aspect, the procedure can be repeated multiple times. In one aspect, the method provides for sequential immunolabeling and erasing of the labels. In one aspect, the method provides for serial multiple antigen colocalization. Methods are also provided for simultaneous visualization of multiple antigens.

In one embodiment, at least two different antigens are detected. In one aspect, at least five different antigens are detected. In another aspect, at least 10 different antigens are detected.

In one embodiment, the present invention provides for the use of multiple immunohistochemical analyses to be performed on otherwise limited tissue samples, such as very small biopsies and tissue microarrays.

One embodiment of the invention comprises compositions and methods that enable sequential immunohistochemical labeling and erasing of a single cell or tissue section with many different primary antibodies, thus allowing, for example, 4, 5, 6, or more antigens to be colocalized in the same cell or tissue sample.

The technique of the invention is called either immunohistochemical Serial Multiple Antigen Colocalization (iSMAC) or Sequential IMmunoPeroxidase Labeling and Erasing (SIMPLE).

Potential compatible substrates for SIMPLE include all those whose precipitated form is non-permanent, such as those soluble in organic solvents. These substrates include, but are not limited to: AEC (3-amino-9-ethylcarbazole), TMB (3,3',5,5'-Tetramethylbenzidine), 4-Cl-1-naphthol, and TrueBlue (TM; KPL, Inc.)

The present invention method or portions thereof can be embodied by manual bench top methods.

The present invention further encompasses the use of an automated slide stainer.

The present invention method or portions thereof is not limited to paraffin sections and may be applied to any slide-based cell or tissue preparation (frozen sections, cytologic smear preparations such as PAP smears or fine needle aspirates).

The present invention method or portions thereof is not limited to peroxidase substrates even though this is the most widely used detection system. Alkaline phosphatase-linked secondary antibodies could be used as long as the substrates are soluble. Such substrates include: NBT/BCIP and AP-Fast Red, among others. Other enzyme-linked immunohistochemical methods including glucose oxidase are compatible with SIMPLE.

The present invention method or portions thereof is not limited to staining with six proteins. Multiple stain colors or substrates can be used each round allowing probing of multiple proteins each round. Furthermore, more rounds can be achieved using a water-immersion objective due to less tissue damage.

The present invention can be used for example, where slides or the substrate on which the tissue or cells are affixed are scanned microscopically, or where there is no scanning. Scanning can be manual or automated and images can be captured digitally and the archived in a computer and processed with a program designed to manipulate images. The size of the area which is scanned or visualized on the slide can be varied.

The present application discloses a method for detecting at least two antigens in a cell or tissue sample, which comprises obtaining a cell or tissue sample, processing the cell or tissue sample for antigen detection, labeling and detecting at least one antigen and optionally capturing an image of the at least one antigen; optionally simultaneously detecting at least two labeled antigens; erasing the label; processing the cell or tissue sample to retrieve the antigen; reprobing the cell or tissue by labeling and detecting at least one different antigen than before, and optionally capturing an image of the different antigen; optionally determining the level of the antigen; and optionally counterstaining the tissue before or after detection of the antigen.

In one embodiment, the cell or tissue is human.

In one embodiment, at least one of the antigens is a protein. In one aspect, all antigens detected are proteins. In one aspect, the proteins include, but are not limited to, Glial Fibrillary Acidic Protein (GFAP), S100-beta, MAP2, Calbindin, Neurofilament protein, Synaptophysin, Adrenocorticotropic Hormone, Thyroid Stimulating Hormone, Luteinizing Hormone, and Human Chorionic Gonadotropin (alpha-subunit).

In one aspect, the label is erased by dissociating an antibody-label complex from the antigen. In one aspect, the processed cell or tissue has been affixed to a substrate. In one aspect, the substrates include, but are not limited to, a slide, a tissue culture chamber slide, a coverslip, a tissue culture dish, and a multiwell plate.

In one embodiment, at least two antigens are detected simultaneously.

In one embodiment, at least two antigens are visualized simultaneously.

In one embodiment, images are captured for at least two antigens. In one aspect, the images are captured separately after consecutive detection of at least two antigens and the images are processed for simultaneous visualization of two or more images captured in said cell or tissue sample.

In one embodiment, at least two antigens are detected in the same cell or tissue.

In one embodiment, the labeling method includes, but is not limited to, immunohistochemical, immunofluorescent, immunogold, and in situ labeling.

In one aspect, the immunohistochemical labeling comprises the use of an enzyme-coupled antibody and a chromogenic substrate. In one aspect, the enzyme is a peroxidase or an alkaline phosphatase. In one aspect, the substrate used includes, but is not limited to, 3-amino-9-ethylcarbazole, 3,3', 5,5'-Tetramethylbenzidine, 4-chloro-11-naphthol, Fast Blue BB, NBT/BCIP, Fast Red, and AP-Fast Red.

In one embodiment, when the substrate is precipitated, the precipitated substrate is non-permanent. In one aspect, the precipitated substrate is soluble in an organic solvent.

In one embodiment, at least five antigens are detected. In another embodiment, six antigens are detected. In yet another embodiment, at least ten antigens are detected. In a further embodiment, at least twenty antigens are detected.

In one embodiment, the cell or tissue is counterstained. In one aspect, the counterstain that can be used includes, but is not limited to, hematoxylin, nuclear fast red, methyl green, and methylene blue.

In one aspect, erasing comprises destaining and antibody stripping.

In one embodiment, the detected antigens are detected in a cell or tissue sample affixed to a slide. In another embodiment, at least two cells or tissue samples are affixed to the slide.

In one embodiment of the invention the method comprises using a whole slide digital scanning microscope, wherein the slide is scanned after the cell or tissue sample is stained or labeled, and a digital image of a stained or labeled cell or tissue sample is captured, and the image is imported into a program for processing images, and optionally one or more images are visualized. In one aspect, the images are processed and overlaid for simultaneous visualization. In one aspect, the program is adjusted to create false-color composites. In one aspect, images of at least two detected antigens are captured.

In a further aspect, at least two images are captured from a cell or tissue sample and are overlaid to form a composite image, optionally using the program to overlay the images, and the composite image is visualized.

In one embodiment, the method comprises sequential immunoperoxidase labeling and erasing.

In one embodiment, the processing of the cell or tissue sample includes, but is not limited to, fixation and paraffin-embedding, freezing, cytologic smears, cytospin preparations, and aspirates.

In one embodiment, various steps of the method can be automated, including the use of automatic slide stainers, automated slide scanning, automatically capturing and processing images, etc. In one aspect, at least two cells or tissue samples are processed simultaneously.

The present invention further provides compositions and methods useful for diagnosing a disease or disorder associated with a change in the level or expression of at least two antigens. The method comprises obtaining a sample from a test subject and comparing the level of at least two antigens in the test subject with the level of the antigens from an otherwise identical sample from an unaffected subject or from an otherwise identical unaffected sample from the test subject. A higher or lower level of the antigens in the sample from the test subject, compared with the levels of the same antigens in a sample from an unaffected subject or from an unaffected sample from the test subject, is an indication that the test subject has the disease or disorder associated with the expression or levels of the antigens. In one aspect, at least five antigens are compared.

Various aspects and embodiments of the invention are described in detail below.

BRIEF DESCRIPTION OF THE DRAWINGS

FIG. 4A comprises five panels. Hematoxylin counterstain (A, left) is used to align subsequent images of hormone labeling (A, right panels) for multicolor display (B), or images can be displayed on a black background (lower right image) to create pseudo-immunofluorescence. Bars=50 μm.

DETAILED DESCRIPTION

Figure 1:
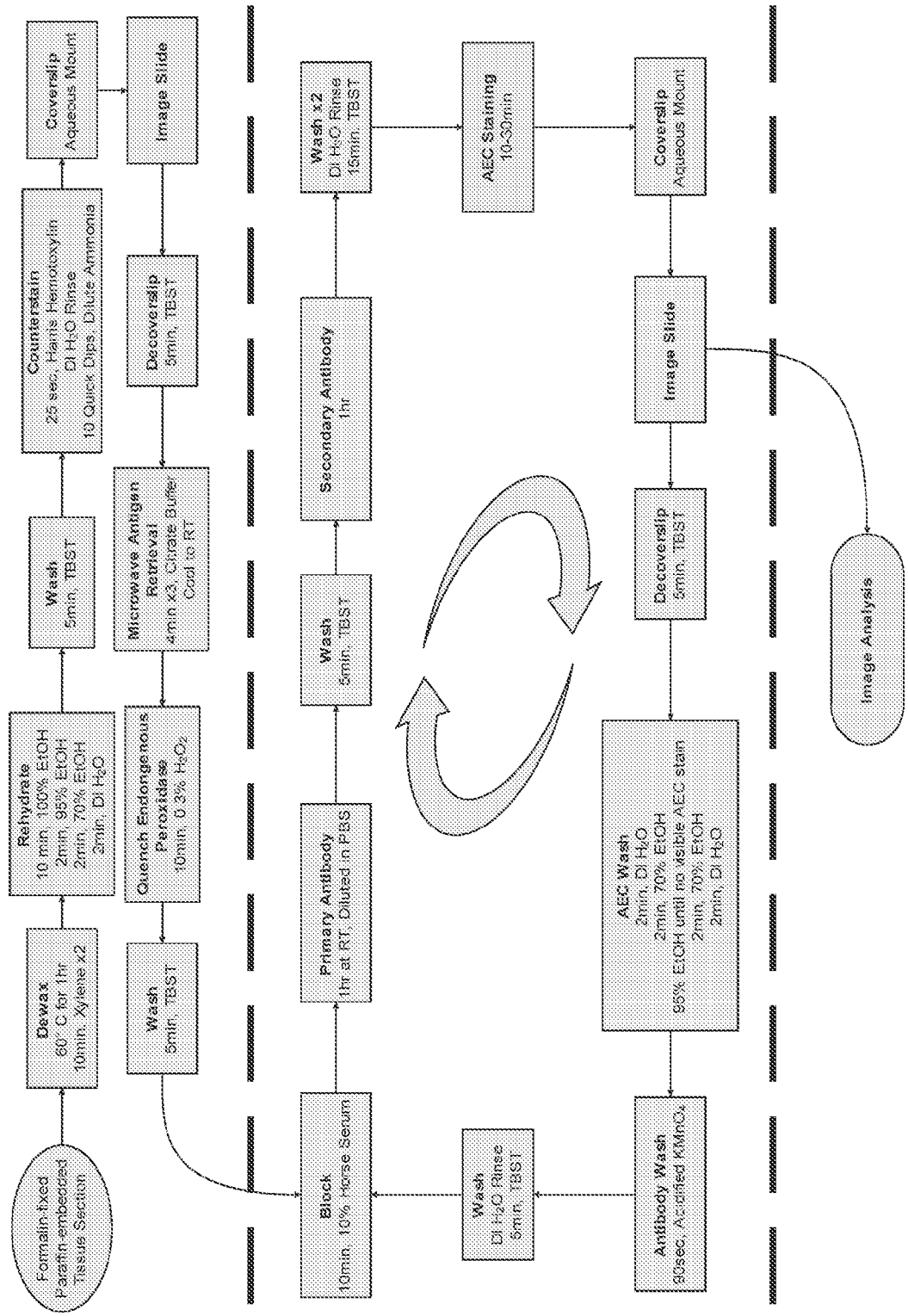
FIG. 1 provides a schematic illustration of the SIMPLE strategy. Formalin-fixed, paraffin-embedded sections are dewaxed, rehydrated, and counterstained before initial probing. Tissue is imaged and then subjected to antigen retrieval, removing the counterstain. Each staining round is conducted using standard IHC protocols with the alcohol-soluble red peroxidase substrate, AEC. After each round of staining, the tissue is imaged and then stripped of AEC precipitate in ethanol. Antibody is then eluted in acidified permanganate and the tissue is subjected to the next round of staining.

Abbreviations and Acronyms
ACTH—adrenocorticotropic hormone
AEC—3-amino-9-ethylcarbazole
GFAP—glial fibrillary acidic protein
hCG—human chorionic gonadotropin alpha subunit
IHC—immunohistochemistry
iSMAC—immunohistochemical Serial Multiple Antigen Colocalization
LH—luteinizing hormone
MELC—multi-epitope-ligand cartography
SIMPLE—Sequential IMmunoPeroxidase Labeling and Erasing
TMA—tissue microarray
TSH—thyroid-stimulating hormone
Definitions In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "affected cell" refers to a cell of a subject afflicted with a disease or disorder, which affected cell has an altered phenotype compared with a subject not afflicted with a disease, condition, or disorder.

Cells or tissue are "affected" by a disease or disorder if the cells or tissue have an altered phenotype relative to the same cells or tissue in a subject not afflicted with a disease, condition, or disorder.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6)

side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

A "biomarker" is a specific biochemical in the body which has a particular molecular feature that makes it useful for measuring the progress of disease or the effects of treatment, or for measuring a process of interest.

By "capturing an image" is meant any technique that can be used to store the detected label, including, but not limited to, capturing photographically an immunohistochemically-detected antigen or a fluorescence-detected antigen, using any photographic or light capturing process, including digital microscopy and photography. This further includes the use and manipulation of the images in programs such as Adobe® Photoshop®.

The term "cell or tissue preparation," as used herein, means any method that isolates or exposes the cell or tissue contents for staining and labeling. A cell or tissue preparation can include, for example, the sections (paraffin or frozen), smears, cytospin preparations, or aspirates, which are prepared using the cell and tissue samples of the invention.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

A "pathoindicative" cell is a cell which, when present in a tissue, is an indication that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

A "pathogenic" cell is a cell which, when present in a tissue, causes or contributes to a disease or disorder in the animal in which the tissue is located (or from which the tissue was obtained).

A tissue "normally comprises" a cell if one or more of the cells are present in the tissue in a subject not afflicted with a disease or disorder.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. However, the definitions of "disease" and "disorder" as described above are not meant to supersede the definitions or common usage related to specific addictive diseases or disorders.

A disease, condition, or disorder is "alleviated" if the severity of a symptom of the disease or disorder, the frequency with which such a symptom is experienced by a patient, or both, are reduced.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

The term "erasing," as used herein, means washing away the solubilized precipitate. For example, an alcohol wash erases the alcohol-soluble peroxidase substrates AEC and CN. Also, alkaline phosphatase substrates such as Fast Red TR and Fast Blue BB are alcohol soluble. The term "erasing" also refers to a method of removing an antibody or label by dissociating it from an antigen and removing any stain or coloration that was present to visualize the antigen, while preserving cell or tissue antigenicity to allow for more antibody-antigen reactions and restaining, or a method of removing the stain or coloration such that the tissue or cell being studied can be reprobed with a different antibody and labeling regimen.

As used herein, a "functional" molecule is a molecule in a form in which it exhibits a property or activity by which it is characterized. A functional enzyme, for example, is one that exhibits the characteristic catalytic activity by which the enzyme is characterized.

The term "inhibit," as used herein, refers to the ability of a compound or any agent to reduce or impede a described function, level, activity, synthesis, release, binding, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein, the term "imaging agent" means a composition of matter which, when delivered to a cell or tissue, facilitates detection of the cell or tissue. Numerous imaging agents are known and described in the literature. By way of example, enzymes, such as β-galactosidase, which are capable of catalyzing a reaction involving a chromogenic substrate may be used. Further by way of example, compounds, the presence of which may be directly detected may be used, such as compounds which emit gamma radiation or which fluoresce, which may be detected using an appropriate detection apparatus.

As used herein, an "instructional material" includes a publication, a recording, a diagram, or any other medium of expression which can be used to communicate the usefulness of the various compositions and methods of the invention. The instructional material of the kit of the invention may, for example, be affixed to a container which contains the identified components of the invention or be shipped together with a container which contains the identified compound. Alternatively, the instructional material may be shipped separately from the container with the intention that the instructional material and the compound be used cooperatively by the recipient.

As used herein, a "labeled antigen" refers to an antigen which has been subjected to a technique such as immunochemistry to allow for its identification or visualization.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is also meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH2-S(O)$_2$NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)$_2$R group, to a —NHC(O)NHR group where R and R1 are hydrogen or C1-C4 alkyl with the proviso that R and R1 are not both hydrogen;

3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

By the term "processing a cell or tissue sample for antigen detection", as used herein, is meant processes such as fixation, embedding in a medium for sectioning, etc., or freezing and processing, or any such method used to prepare cells or tissues for the steps of detecting an antigen. It does not necessarily include the antibody binding and staining or fluorescence steps themselves.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

A "receptor" is a compound or molecule that specifically binds to a ligand.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample also refers to cells, tissue, etc., which have been grown in cell or tissue culture conditions, or have been processed outside the subject before being used in the invention. The present invention further encompasses cells and tissues derived from plants and organisms other than mammals.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample.

By the term "specifically binds," as used herein, is meant a molecule which recognizes and binds a specific molecule, but does not substantially recognize or bind other molecules in a sample, or it means binding between two or more molecules as in part of a cellular regulatory process, where said molecules do not substantially recognize or bind other molecules in a sample.

The term "standard," as used herein, refers to something used for comparison. For example, it can be a known standard agent or compound which is administered or added and used for comparing results when adding a test compound, or it can be a standard parameter or function which is measured to obtain a control value when measuring an effect of an agent or compound on a parameter or function or for detecting a target. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of diagnosis or treatment is a plant or animal, including a human. Non-human animals subject to diagnosis or treatment include, for example, livestock and pets.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "target molecule" refers to molecules such as antibodies or other antigens detectable by the present invention.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "visualizing an antigen" refers to any method that allows for identifying the presence of an antigen various imaging techniques and with various automated techniques to allow for comparison of multiple antigens that have been detected, for comparison of exact location of the antigen, etc., and includes the process of capturing images, such as by photography, including digital photography, exporting the images to a computer or server, and overlaying images, including using computer programs designed for image processing.

The present invention further encompasses the use of various techniques for determining the levels of each detected antigen and for comparison with other tissues or cells or with standards.

EMBODIMENTS

The ability to simultaneously visualize expression of multiple antigens in cells and tissues can provide powerful insights into cellular and organismal biology. However, standard methods are limited to the use of just two or three simultaneous probes and have not been widely adopted for routine use in paraffin-embedded tissue.

The present invention allows for analyzing multiple targets in a reasonable amount of time, but because there is a wide range in the timing of antibody incubations and washes, the number of antigens being targeted, etc., the amount of total time required for the whole process can vary. The present invention usually requires about 1-2 hours per round, resulting in 5-10 hours for a 5 antigen experiment. There is also a range of time for scanning each stain, depending on speed of scanner, etc.

The present invention as described below, wherein a large area is scanned on the exemplified tissue sample on a slide, can be adapted to allow multiples of the current probe numbers. For example, the present invention can be coupled with other methods, such as those described in J. Histochem. and Cytochem. (2004, 52:2:205-210) which demonstrates staining of a single tissue section with an array of spot-applied antibodies, using up to 50 antibodies per run. Coupling that method with the present invention (SIMPLE) could multiply the 50 probes used in that publication by 10 or more fold.

One embodiment of the invention is summarized in FIG. 1.

The present invention encompasses compositions and methods for simultaneously visualizing at least two different markers (antigens) in a sample by contacting a test sample suspected of having the at least two different markers with at least two different antibodies directed against those markers, i.e., a first antibody and a second antibody, adding a reagent which can be processed for detection and visualization, and then stripping/eluting the antibodies and repeating the process. Controls and processes are provided to allow simultaneous visualization of all markers tested. In one aspect, markers can be detected simultaneously and the images can be captured simultaneously. In another aspect, markers are detected serially and once they have been detected and images captured and stored, they can then be visualized simultaneously. In one aspect, at least 5 serial procedures can be done. In another aspect, at least 10 serial procedures can be performed. In another aspect, at least 15 serial procedures can be done. In yet another aspect, at least 20 serial procedures can be done. In yet another aspect, at least 25 serial procedures can be done. One of ordinary skill in the art will understand that the number of serial or sequential stains and labeling performed, including a counterstain, can vary depending on the processes used and can be increased by such things as gentler slide handling and washing methods. In one aspect, multiple antigens can be detected. In one aspect, multiple antigens can be visualized.

Although the present invention provides exemplifications for serial stripping, reprobing, detection, and simultaneous visualization of multiple antigens, the present invention is also compatible with other methods for increasing the number of antigens being visualized or probed at a time. For example, the number of antigens studied could be doubled by employing two-color IHC, using standard methods. In one embodiment, this could be performed with a peroxidase substrate such as AEC plus an alkaline phosphatase substrate, such as Fast Blue BB. Using different species of primary antibodies (e.g., mouse and rabbit) allows easy double staining.

In one embodiment, the present invention provides compositions and methods that allow for sequential immunohistochemical labeling and label erasing of a single tissue section with many different primary antibodies, thus allowing 2, 3, 4, 5, 6, or more antigens to be colocalized in the same cell or tissue. In one aspect, erasing comprises destaining and antibody stripping.

Immunochemistry detects target molecules through antigen-antibody complexes in tissue and cell samples using enzyme-linked antigens or antibodies. The presence of the target molecule is detected via an enzyme immunoassay.

The present invention is not limited to methods such as immunohistochemistry for the detection system. Various methods for detection include, but are not limited to, fluorescence, immunoperoxidase, immunogold, and in situ methods.

In one embodiment, the present invention is also useful for in situ hybridization.

SIMPLE is greatly facilitated by the use of a whole slide scanner, which can capture the results of each sequential stain without any information loss. Other automated systems are also adaptable for use with the present invention.

The technique of the present invention is called either immunohistochemical Serial Multiple Antigen Colocalization (iSMAC) or Sequential IMmunoPeroxidase Labeling and Erasing (SIMPLE) herein.

Potential compatible substrates for SIMPLE include all those whose precipitated form is non-permanent, such as those soluble in organic solvents. These include but are not limited to: AEC (3-amino-9-ethylcarbazole), TMB (3,3',5,5'-Tetramethylbenzidine), 4-Cl-1-naphthol, and TrueBlue (TM; KPL, Inc.)

The present invention further provides compositions and methods that can be practiced using manual bench top methods.

The present invention encompasses the use of an automated slide stainer, including, but not limited to, those marketed by DAKO, Ventana, and others.

In one aspect, the present invention encompasses the use of an integrated automated slide stainer/scanner, that can acquire microscopic resolution scans of each stain prior to the erasing steps, as well as archiving the data to a server. In one aspect, the use of a water-immersion objective lens system obviates the need for coverslipping of the slides after each staining round, and increases the number of rounds of staining possible without damaging tissue.

In another embodiment, the present invention may extend the probe/erase concept beyond slide-based staining to high-throughput plate-based immunostaining and immunocytochemical assays ("in-cell Westerns"). Many drug screens are now carried out using cellular morphological readouts and the ability to sequentially probe the same set of treated cells with different antibodies should be widely desirable.

The present invention is not limited to paraffin sections and may be applied to, for example, any slide-based cell or tissue preparation, including, but not limited to, frozen sections, cytologic smear preparations such as PAP smears or fine needle aspirates.

The present invention is not limited to peroxidase substrates even though this is the most widely used detection system. Alkaline phosphatase-linked secondary antibodies could be used as long as the substrates are soluble. Such substrates include: NBT/BCIP and AP-Fast Red, among others. Other enzyme-linked immunohistochemical methods including glucose oxidase are compatible with SIMPLE.

The methods of the present invention are not limited to staining with a fixed number of proteins, such as six proteins. Multiple stain colors or substrates can be used each round allowing probing of multiple proteins each round. Furthermore, more rounds can be achieved using a water-immersion objective due to less tissue damage.

The type of staining and substrates may vary according to the types of cells and tissues being examined. For example, peroxidase substrates are sometimes preferred for neural tissue because they provide more consistent labeling of both cell body and processes. Optionally, a second antigen may be processed for visualization before the antibodies against the first antigen are eluted and before the color is washed away for the substrate whose color was developed for the first antigen visualization. In one aspect, two antigens can be processed at the same time and simultaneously visualized. This is particularly useful when the two antigens are not in the same cellular compartment. Examples of such are provided in the instructions for use with Vector Laboratories kits.

Target Molecules and Antigens

The present invention is not limited to the specific proteins exemplified in the examples below, such as Glial Fibrillary Acidic Protein (GFAP), S100-beta, MAP2, Calbindin, Neurofilament protein, Synaptophysin, Adrenocorticotropic Hormone, Thyroid Stimulating Hormone, Luteinizing Hormone, and Human Chorionic Gonadotropin (alpha-subunit). The present invention additionally encompasses the use and study of all types of proteins and fragments thereof where an antibody can be used to bind with that protein or fragment thereof. For example, the various types of proteins included in the present invention include, but are not limited to, cell differentiation markers, Cluster Designation immunological markers (CD1-CD166), cytoskeletal proteins, G protein-coupled receptors, ion channels, receptor tyrosine kinases, oncogenes, tumor suppressor proteins, cell cycle regulators, kinases, phosphatases, nuclear receptors including estrogen and progestin receptors, transcription factors, proteases, cell adhesion proteins, nuclear membrane proteins, golgi apparatus proteins, endoplasmic reticulum proteins, mitochondrial proteins, and lysosomal proteins.

In one embodiment, other methods can be combined or useful with the present invention. The present invention can be coupled with other methods, for example, to ensure reliable enzymatic or fluorescent staining without cross-reactivity and without loss of tissue antigenicity, thus offering a flexible tool for colocalization studies and pathological diagnosis.

Biological Samples—Tissues and Cells

The methods of the present invention are not limited to the tissues exemplified in the examples. In one aspect, other tissues and methods include, but are not limited to, the study or other formalin-fixed cells and tissues, as well as fresh-frozen cells and tissues. For example, tissues include, skin, hepatic, carcinomas such as breast, oral, and gastric carcinomas, and other types of tumors. Fresh-frozen tissues useful for the present invention include, but are not limited to, liver, lymph node, and breast tissue sections.

The present invention provides for the use of biopsies as tissue samples. Biopsies include both tumor and non-neoplastic processes affecting skin (melanomas, carcinomas, etc.), soft tissue, bone, hematopoietic, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle. The present invention further encompasses research or toxicology testing of animal tissues named herein or any others that can be processed and analyzed using the methods of the present invention.

The present invention allows simultaneous detection of multiple target molecules on the same sample. In one aspect, the sample is a pathological specimen. Target molecules include, but are not limited to, antigens, including antigens derived from microorganisms and other pathogens, antibodies produced in response to those antigens, tumor markers, proteins, receptors, DNA, RNA and any artificial nucleic acid molecules, fragments or probes, or other oligonucleotides, and self-antibodies generated in autoimmune disease. In one aspect, a target molecule is a biomarker. In one aspect, the biomarker is a useful marker for diagnosing a disease or disorder associated with the expression or level of the biomarker, or for monitoring the progression or treatment of a disease or condition associated with the expression or level of the biomarker. In one aspect, multiple biomarkers can be used.

Biological samples and specimens, including pathological samples, include but are not limited to, a histological tissue section and/or other biological preparations such as tissue culture cells, Cytospin preparations, and PAP smears. In one aspect, a visualization technique such as flow cytometry may be required for cells in suspension.

Modifications

One of ordinary skill in the art will also appreciate that for certain conditions or for certain antigens, cells, or tissues to be tested, the methods can be modified. For example, other antibody elution techniques are encompassed by the invention when the methods are modified. In one aspect, a variety of antibody elution (stripping) buffers have been described in the literature, and could be useful with the present invention. For example, the glycine SDS pH 2 buffer as described by Pirici et al. could be used when modifying the present invention (Pirici et al., 2009, J. Histochem. Cytochem., 57:567-575). In one aspect, formamide can be used to elute antibodies (Caruccio et al., 2002, Vox Sanguinis, 83:63-96).

In one embodiment, other embedding methods can be used instead of paraffin for fixed tissue. In one aspect, alternative embedding media include, but are not limited to, polyester wax, polyethylene glycol, acrylic resins, and epoxy resins.

In one embodiment, fixatives other than formalin can be used. Other useful fixatives include, but are not limited to, paraformaldehyde, methanol, ethanol, acetone, or any other fixative that is compatible with preservation of antigens of interest.

Also, tissue can be snap-frozen without fixation in a freezing medium such as Tissue-Tek® O.C.T. or TFM™ and sectioned unfixed on a cryostat (as is done in the surgical pathology laboratory for intraoperative frozen sections).

In one embodiment, tissue or cells can be frozen without fixation and subjected to cryosectioning. Examples of cryo-sectioning embedding media for frozen sections, include Tissue-Tek® O.C.T. or TFM™.

In one aspect, the present invention can be modified to use immunofluorescence labeling. In one aspect, indirect immunofluorescence can be used. In one aspect, the methods can be coupled with confocal laser scanning microscopy.

One of ordinary skill in the art will appreciate that the present invention can also be practiced using tissue microarrays.

Other compositions and methods useful for the practice of the invention that are not described herein can be found for example, in U.S. patent application Ser. No. 12/606,309 (Tacha et al.) or U.S. patent application Ser. No. 09/947,726 (Damaj et al.).

Combinations

In one embodiment of the present invention, compositions comprising two or more antibodies mixed with various reagents are provided. In one aspect, the present invention provides compositions comprising reagents suitable for the detection of the antibody containing reagents are provided. In another aspect of the present invention, methods of detecting two or more antigens in a single sample using the compositions of the invention are provided.

Processes and Automation

In one embodiment, the method can be performed on an automated device capable of staining and detecting the antigens in the sample. Compositions comprising reagents suitable for the detection of the antibody containing reagents are provided.

The compositions and methods of the present invention are useful for any method where antibody staining is conventionally employed. For example, double, triple and quadruple staining can be performed using immunocytochemistry; immunohistochemistry; frozen sections; formalin-fixed paraffin embedded tissues; cell cultures; tissue or cell culture microarrays; paraffin-embedded tissues (any fixation protocol); cell smears; cell blocks; Cytospins; PAP smear; blood smears; and touch preps. In certain embodiments, the sample can be attached to a solid support, for example, a glass slide, ELISA plate, culture dish, glass dish, plastic dish, glass well, or plastic well.

In one embodiment, the present invention provides methods for identifying pathogens. For example, Chlamydia and gonorrhea infections are often coincident in women.

The present invention allows for the detection of multiple antigens simultaneously in the same sample. Similarly, the detection, diagnosis and monitoring of cancers such as prostate cancer can be assisted with the screening of additional markers. For example, prostate specific antigen ("PSA") is normally produced by the body. Thus, a mildly increased PSA level is insufficient to support a diagnosis of cancer, but the absence of a basal cell layer is a well accepted criterion for diagnosis of prostate carcinoma. However, it can be difficult to identify this cell layer on standard histological examinations. The present invention permits the simultaneous detection of PSA and high molecular weight keratin on the same histological sample, as well as other markers in that sample. Any molecule that an antibody can be directed against is a potential target molecule.

The present invention further provides for the use of two or more primary antibodies in a cocktail. In one embodiment, the antibody compositions or cocktails of the present invention comprise two or more antibodies in double staining procedures, and, for example, in triple staining procedures the compositions would contain three antibodies, etc. The antibodies can be monoclonal or polyclonal and can be obtained according to standard antibody technology known in the art. The antibodies can be from any species, such as rat, horse, goat, rabbit, human, mouse, etc. In one aspect, the at least two of the antibodies in the composition are from different sources or species. In another embodiment, at least one of the antibodies in the primary antibody cocktails is a rabbit antibody, and more preferably a rabbit monoclonal antibody.

The antibodies can be diluted in one or more of the buffer systems described herein, for example, at least 1:50 and preferably from about 1:50 to 1:6000, including 1:100, 1:150, 1:200, 1:250, 1:300, 1:350, 1:400, 1:450, 1:500, 1:550, 1:600, 1:650, 1:700, 1:750, 1:800, 1:850, 1:900, 1:1000, 1:1100, 1:1200, 1:1300, 1:1400, 1:1500, 1:1600, 1:1700, 1:1800, 1:1900, 1:2000, 1:2100, 1:2200, 1:2300, 1:2400, 1:2500, 1:2600, 1:2700, 1:2800, 1:2900, 1:3000, 1:3100, 1:3200, 1:3300, 1:3400, 1:3500, 1:3600, 1:3700, 1:4000, 1:4100, 1:4200, 1:4300, 1:4400, 1:4500, 1:4600, 1:4700, 1:4800, 1:4900, 1:5000, 1:5100, 1:5200, 1:5300, 1:5400, 1:5500, 1:5600, 1:5700, 1:5800, 1:5900 and all ranges and values therebetween. One of ordinary skill in the art can determine which dilutions to use.

In one embodiment, the two or more antibodies are prepared in a composition comprising a buffer system that stabilizes the antibodies and facilitates a faster detection after the antibodies have bound to the antigen.

In one embodiment, the secondary antibodies react with the primary antibody based on the species origin of the primary antibody, e.g., if the primary antibody is a mouse antibody then the secondary antibody would be, for example, a rabbit anti-mouse antibody. In the present invention, the two or more secondary antibodies to visualize the binding between the two or more primary antibodies and the two or more antigens may be from the same source species or from different species. However, the two or more secondary antibodies are preferably coupled to a detectable moiety. In one aspect, each of the at least two secondary antibodies has a different detectable moiety. In another aspect, each of the at least two secondary antibodies has the same moiety.

In one embodiment of the present invention, chromogens are used to detect the antibody-antigen complex. Newer chromogens are permanent and do not fade. They come in several different colors. In one aspect, multiple different chromogens on a single section can be used. For example, chromogens useful in HRP Systems include, DAB (which appears brown), AEC (which appears brick red), and Bajoran Purple (which appears lavender to dark purple). Chromogens useful for Alkaline Phosphatase Systems include Fast Red (which appears pink to fuchsia), and Ferangi Blue (which appear royal blue).

In one embodiment, counterstains can used to visualize the staining patterns of the antibody-antigen complex. Non-limiting examples of those counterstains include hematoxylin (as described in detail below), nuclear Fast Red, methyl green, and methylene blue. Alternatives to acidified permanganate could include many acidic buffers. It is important to note that the "SIMPLE" invention as described herein is not limited to peroxidase-coupled immunohistochemistry. It can be used for alkaline phosphatase-coupled immunohistochemistry with the alcohol-soluble substrate, Fast Red TR and Fast Blue BB. Other alcohol-soluble peroxidase substrates include 4-chloro-11-naphthol (CN).

The present invention can also be used with various automated applications, in addition to the slide scanning method described in the examples. The unique formulations and ease of use of the antibody cocktail and/or detection reagents and/or other regents useful for the immunoassay of the invention facilitate performing the immunoassay in one or more automated devices designed to detect antibody staining patterns in a sample. In one aspect, the compositions of the present invention enable automation of double, triple, quadruple, etc. antibody detections.

In another embodiment of the invention, the method described herein can be applied in the immuno-analysis of tissue microarrays. Tissue microarrays are known in the art and typically contain anywhere from 50 to 500 tissues on a single slide. The advantage of the present invention in the immuno-analysis of the tissue arrays is that the assay can be performed on numerous slides, e.g., 36 to 60 slides, on an automated staining apparatus and perform double, triple, quadruple, etc. stains on each slide. Another advantage of being able to perform such multiple stains on a given slide is cost savings and need for less sample. Another advantage of the present invention is the use of whole slide scanning to capture images and the use of automated processes.

Automated devices and procedures useful in the practice of the present invention include, but are not limited to, BioGenex 16000™, (Biogenex), Dako Autostainer (DakoCytomation) Nemesis™ (BIOCARE), and those from Ventana Medical Systems (Capillary gap stainer, NexES and Benchmark).

In one embodiment, the methods of the invention include use of a whole slide digital scanning microscope, scanning the slide, taking a digital snapshot of the slide using an appropriate device, importing the snapshots into a program for processing images (for example, Adobe Photoshop), optionally overlaying the images, optionally adjusting to create false-color composites, and optionally visualizing all overlaid images simultaneously.

EXAMPLES

In order to overcome the limitations described in the Background, described herein is a novel approach called Sequential IMmunoPeroxidase Labeling and Erasing (SIMPLE) that enables the simultaneous visualization of multiple markers within a single tissue section. By combining the use of an alcohol-soluble immunoperoxidase substrate, 3-amino-9-ethylcarbazole (AEC), with a previously described antibody-antigen dissociation method (6), we have performed up to five serial rounds of staining on a single tissue section without loss of tissue antigenicity. This method is accessible to any histology lab and requires no specialized equipment. The use of a whole slide digital scanning microscope greatly increases the power of SIMPLE as it facilitates permanent archiving of each round of labeling. In addition, from a practical standpoint, the method enables multiple immunohistochemical analyses to be performed on otherwise limited tissue samples, such as very small biopsies and tissue microarrays.

Materials and Methods

Tissue Samples

Mice were perfused intracardially with 4% paraformaldehyde after deep anesthetization with xylazine/ketamine. After overnight fixation in 4% paraformaldehyde, brains were then embedded in paraffin and sectioned at 4 μm. Human pituitary tissue was obtained from autopsy-procured archival specimens.

Antibodies

The following primary antibodies were used: GFAP (DAKO rabbit polyclonal #Z0334, 1:5000); 510043 (DAKO rabbit polyclonal Z0311, 1:500); calbindin (Sigma mouse monoclonal C8666, clone CL300 1:1000); neurofilament-M (monoclonal antibody, clone 5B8, Developmental Studies Hybridoma Bank, University of Iowa, supernatant used undiluted); MAP2 (NeoMarkers monoclonal antibody AP18, 1:500); adrenocorticotropic hormone (ACTH; DAKO mouse monoclonal antibody clone 02A3, 1:4000); human chorionic gonadotropin alpha subunit (hCG; mouse monoclonal antibody, Biogenix clone F23, 1:25); luteinizing hormone (LH; DAKO mouse monoclonal antibody clone C93, 1:400); thyroid-stimulating hormone (TSH; Biogenix mouse monoclonal antibody clone 5404, 1:400).

Immunohistochemistry

Paraffin sections mounted on slides were placed in a 60° oven for one hour, then dewaxed in xylenes (5 min×2) and rehydrated in a series of graded alcohols to distilled water. Prior to immunostaining, the tissue was stained with hematoxylin followed by bluing in 0.5% ammonium hydroxide. Slides were then coverslipped in aqueous mountant (70% glycerol in PBS or GelMount; Genetex, San Antonio, Tex.). After slide imaging (see below), slides were decoverslipped by immersion in distilled water and rinsed in TBST. One round of antigen retrieval was then performed, consisting of three cycles of five minutes (high power) in a commercial microwave in 10 mM sodium citrate buffer (pH 6.0), followed by cooling to room temperature. Endogenous peroxidase was quenched in 3% hydrogen peroxide for 10 minutes, followed by rinsing in TBST. Tissue was then blocked in 2.5% normal horse blocking serum (Vector Laboratories, Burlingame, Calif.) for 20 minutes, followed by a one-hour incubation of primary antibody at room temperature. Detection of primary antibody was performed with the ImmPress reagents for either mouse or rabbit primaries (DAKOCytomation) and the peroxidase substrate 3-amino-9-ethylcarbazole (AEC; Vector Laboratories), and slides were again coverslipped in aqueous mounting medium.

AEC Destaining and Antibody Stripping

After high resolution scanning, slides were decoverslipped in distilled water and stained slides were dehydrated in an alcohol gradient to 95% ethanol. Slides were incubated until no visible AEC reaction product remained. Following rehydration, antibodies were eluted by incubating sections in 0.15M $KMnO_4$/0.01M $H_2SO_4$ solution for two minutes, followed immediately by a distilled water wash (6). Tissue was then restained, beginning with the blocking step, as described above.

Microscopy and Image Analysis

Full slide scans of stained tissue were obtained after each round of staining on an Aperio ScanScope at 40× magnification (Aperio Technologies, Vista, Calif.). To make multicolor composite images, digital snapshots of tissue section subregions were selected and overlaid as separate layers in Adobe Photoshop CS2 (Adobe Systems, Inc., San Jose, Calif.). The hematoxylin-stained image was used as the background layer. Working with a single layer at a time, subsequent layers were aligned to the background image by selecting the "difference" blending mode and using the "move tool" to nudge the layer into proper alignment. Aligned layers were then linked to prevent further movement. Alignment of all layers was confirmed by visual inspection using the "normal" blending mode and toggling between layers. The "select color" tool was then used to copy the stained regions of each image into a new layer. The "replace color" tool was then used to selectively apply pseudocolors to replace the AEC precipitate color. These psuedocolored layers were overlaid using the "normal" blending mode to produce the final composite images.

Results

SIMPLE Strategy

The general protocol of the SIMPLE method is illustrated in FIG. 1. Formalin-fixed, paraffin-embedded tissue is dewaxed and rehydrated using standard procedures. The tissue is subsequently counterstained with hematoxylin, and a counterstain-only reference image is obtained. Following imaging, antigen retrieval is performed, which also removes the counterstain. This retrieval is followed by immunohistochemical staining with the red peroxidase substrate 3-amino-9-ethylcarbazole (AEC). After imaging, the AEC precipitate is washed away in 95% ethanol and bound antibody is removed in an elution solution of acidified $KMnO_4$. The staining process is then repeated as desired, with subsequent images analyzed separately or overlaid digitally using pseudocoloring to form a single composite image. The method is greatly facilitated by use of a whole-slide scanning microscope, which provides permanent archiving of all labeling and allows any region of each stain to be viewed at a variety of magnifications.

The steps do not necessarily need to be performed in this order. For example, elution of bound antibody could be performed before washing away AEC and in some cases elution of the bound antibody may also wash away the precipitated AEC, eliminating the need for the AEC wash.

Validation of Antibody Removal and Antigen Preservation

Figure 2:
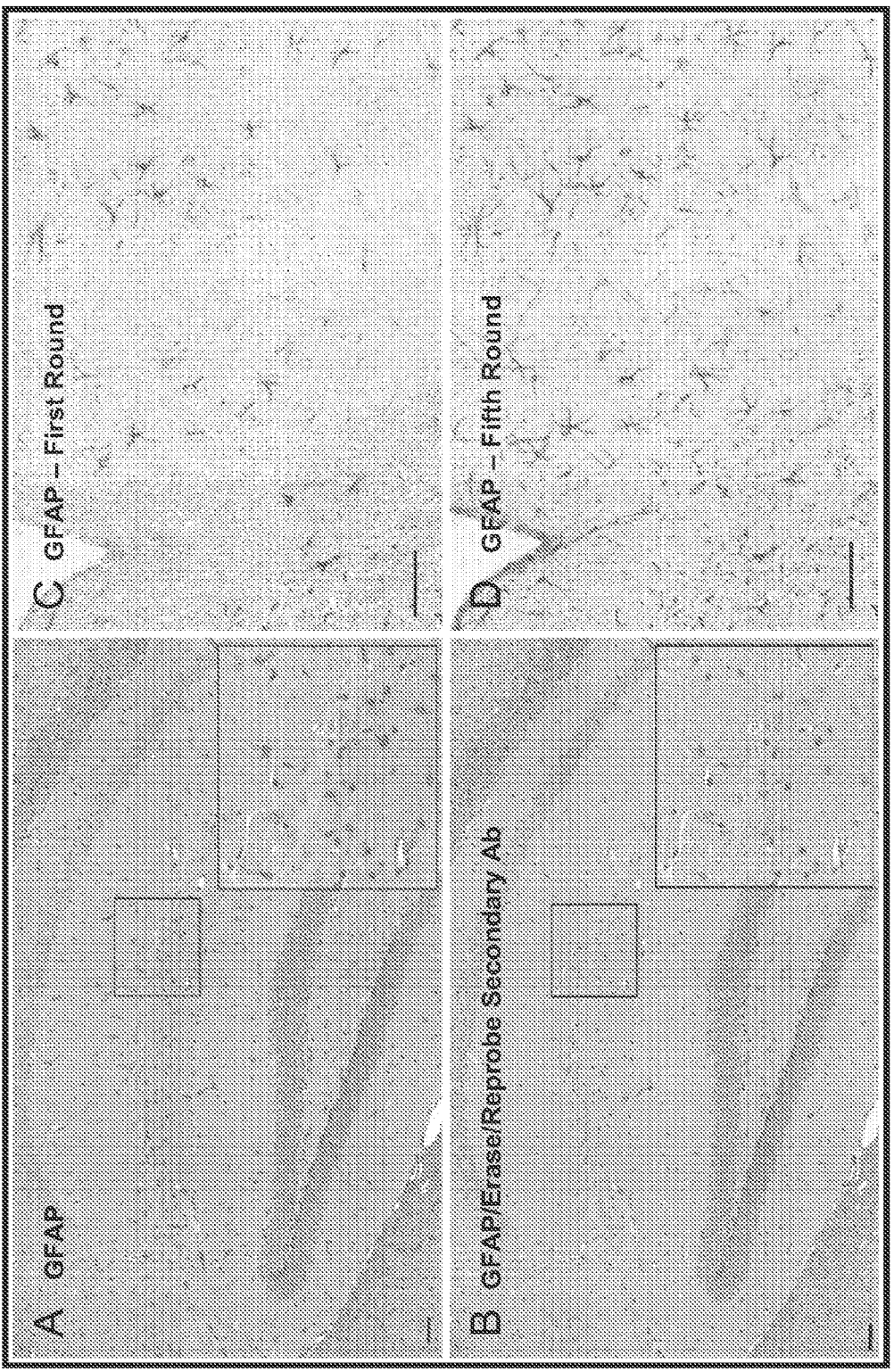
FIG. 2, comprising FIGS. 2A-2D, comprises images of four micrographs, illustrating the antibody elution efficacy and preservation of tissue antigenicity after five rounds of SIMPLE. Adult mouse brain was probed for GFAP and imaged (A). After stripping and antibody elution, the tissue was incubated in secondary antibody and AEC according to standard IHC protocol. Corner inset shows enlargement of small boxed region. Counterstaining in hematoxylin was performed, and the tissue was then imaged again (B). A complete lack of staining was observed, indicating that the primary anti-GFAP antibody had been completely eluted. Corner inset shows enlargement of small boxed region. A section of adult mouse brain was probed for GFAP, both initially (C) and again after four previous rounds of SIMPLE (D). GFAP immunostaining was completely retained and in fact appeared more intense. Bars=50 µm.

In order to validate the efficacy of acidified permanganate as an antibody-stripping agent, an adult mouse brain section was immunostained with a rabbit anti-GFAP polyclonal antibody, imaged, and then treated with acidified permanganate. The section was then blocked and incubated in peroxidase-conjugated anti-rabbit secondary antibody for 1 hour, followed by 30 minutes of incubation in AEC substrate. After re-counterstaining, the tissue was imaged again and analyzed for the presence of any residual anti-GFAP antibody. A complete lack of staining was observed, indicating a complete removal of bound primary and secondary antibody (FIG. 2A-B). A test of antigen stability was performed by subjecting a single mouse brain section to five stain-strip cycles, reprobing for GFAP each time. GFAP immunoreactivity actually became more intense following several rounds of staining and elution, possibly due to an antigen retrieval effect of the acid treatment (FIG. 2C-D).

Multiple Antibody Visualization

Figure 3:
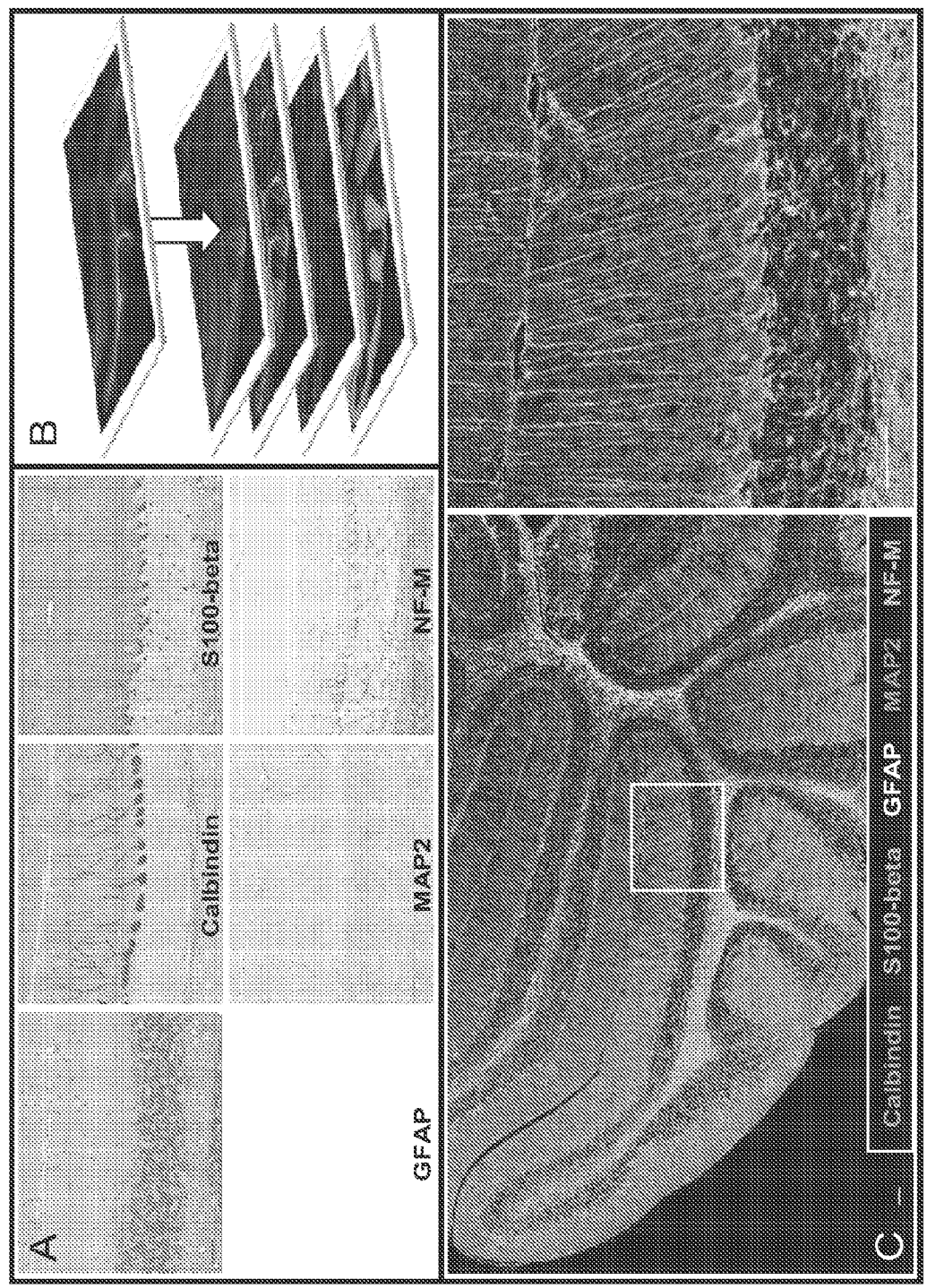
FIG. 3, comprising FIGS. 3A-3C, provides images of micrographs depicting the simultaneous visualization of five probes in mouse cerebellum. Adult mouse brain was counterstained with hematoxylin, then sequentially probed with polyclonal antibodies to calbindin, S100-β, and GFAP, and monoclonal antibodies to MAP2 (AP18), and neurofilament (2H3) (A). The images were individually pseudocolored and overlaid (B). The resultant image (C) reveals the morphology of different cell types and reveals fine details of interactions of Purkinje cells, Bergmann glia, astrocytes, and basket cell terminals that would not be obvious with single or dual labeling. The small boxed area in the left panel (C) is shown magnified at right. Bars=50 μm.

To demonstrate the ability to probe for multiple antigens on a single tissue section, a sagittal mouse brain section was stained with antibodies recognizing calbindin, S100-β (rabbit polyclonal), GFAP (rabbit polyclonal), MAP2 (mouse mAb AP18), and neurofilament (mouse mAb 2H3) (FIG. 3A). Digital snapshots of the same brain regions were taken from each slide scan. Snapshots were imported into Adobe Photoshop (Adobe Systems, Inc., San Jose, Calif.) and overlaid, and the "Replace Color" tool was used to create a false-color composite allowing for simultaneous visualization of all five probes (FIGS. 3B and 3C). In the cerebellum, Purkinje cells stained strongly for calbindin, and they also contained dendritic MAP2. S100-β and GFAP were seen to colocalize in astrocytes and Bergmann glia, with robust expression in the nucleus and processes, respectively. Neurofilament staining revealed axons, especially those of basket cells terminating on Purkinje cell bodies.

Figure 4:
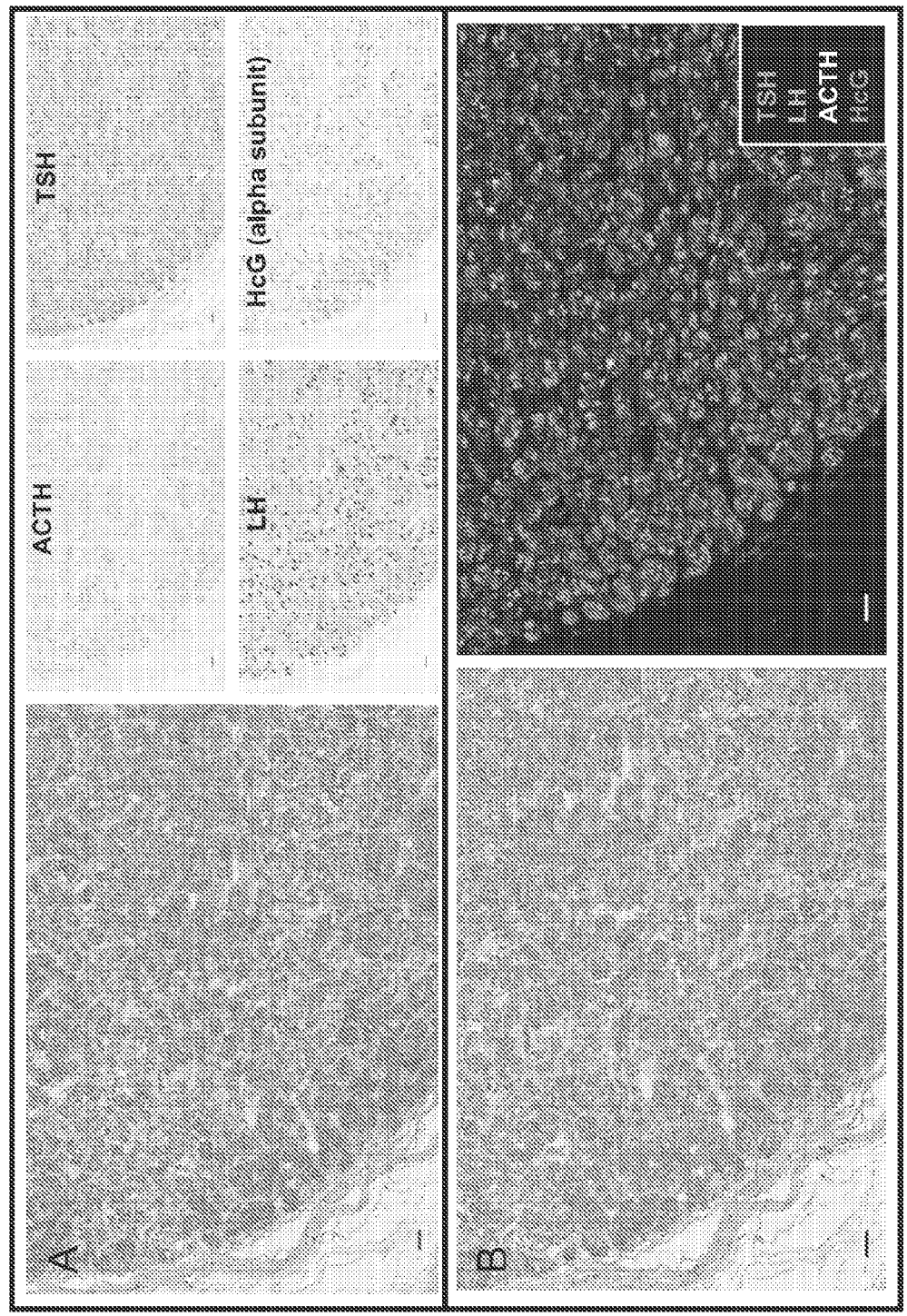
FIG. 4, comprising FIGS. 4A and 4B, provides images of photomicrographs of SIMPLE labeling of hormone expression in human anterior pituitary. Paraffin-embedded human anterior pituitary was probed for ACTH, LH, hCG, and TSH, respectively.

To ascertain the utility of the SIMPLE method for use on human archival tissue, autopsy pituitary tissue was obtained. SIMPLE imaging for ACTH, hCG, LH, and TSH was performed (FIG. 4A). The pseudocolored image allows clear visualization of all probes, revealing patterns of unique and overlapping hormone expression (FIG. 4B).

SIMPLE was compared with existing multiprobe immunolabeling methods. In Table 1 is a comparison of SIMPLE with traditional 2 or 3-color peroxidase IHC, the multiplex immunostain chip method (5), and multicolor immunofluorescence methods.

TABLE 1

Comparison of SIMPLE with existing multiprobe immunolabeling methods

| | SIMPLE | Traditional IHC Multicolor Methods | Multiplex-Immunostain Chip | Multicolor IF |
|---|---|---|---|---|
| Maximum Labels Per Section | 5+ | 2-3 | 50 | 3 |
| Use on Paraffin-Embedded Archival Tissue | + | + | + | -/+ |
| Avoids Autofluorescence/Photobleaching | + | + | + | - |
| Colocalization within a Single Cellular Compartment | + | - | - | + |
| Compatible with primary antibodies from same species | + | - | + | - |

Conclusions

The technique of stripping bound antibody from antigen is widely used to reprobe Western blots and has been used previously to improve multistain immunoenzyme methods (6). However, SIMPLE is a novel approach to eliminate the problems associated with multi-probe color compatibility and antigens located in the same cellular compartment. The advent of new, whole-slide scanning technologies combined with the use of alcohol-soluble peroxidase substrates such as AEC creates a powerful tool for multiple antigen colocalization in paraffin-embedded tissue. Here we have validated antibody removal and antigen preservation, and demonstrated the ability to apply SIMPLE on single paraffin sections from mouse or human.

Traditional multiple immunofluorescent staining is generally limited by the number of different primary antibody species (i.e., mouse, rabbit, goat) that would allow specific labeling of each primary. As a consequence, typically only two or three distinct colors may be stained. Recent approaches have allowed multiple labeling with antibodies from the same species, although they have not found widespread utility (7). For multiple immunoperoxidase labeling, there is the additional limitation that opaque substrates do not allow simultaneous visualization within the same subcellular compartment, such as the nucleus.

A related method, termed MELC (multi-epitope-ligand cartography) offers the ability to image the localization of dozens of antigens in the same cell or tissue preparation, using a sequential immunofluorescence method with a photobleaching erasing step (8). MELC is a powerful technique that will likely provide novel insights into multiple protein colocalization patterns. However, an important disadvantage of MELC as compared with SIMPLE is that the photobleaching step in MELC can only be applied to the microscope's field of view, meaning that the multi-probe image is limited to a single microscopic medium-to-high power field. In contrast, SIMPLE, when imaged using a whole-slide scanner, provides a mulitprobe image for the entire tissue section, which encompasses thousands of high-power fields. Another disadvantage of MELC is cost: the method requires a robotic staining apparatus integrated with an inverted fluorescence microscope. Finally, the reliance of MELC on immunofluorescence can be a problem in some archival fixed human tissues that contain high levels of tissue autofluorescence.

Situations in which tissue specimens are limiting in quantity could benefit from SIMPLE. In clinical consultations, pathologists are frequently provided inadequate numbers of unstained slides to perform a full array of immunohistochemical stains. Likewise, tissue microarrays (TMAs) are often limited in availability, and when they are obtained commercially, are often very costly. In both these instances, the tissue samples could be probed with multiple antibodies using SIMPLE. An important advantage of a serial immunohistochemical approach is that the same cells or tissue feature can be analyzed for expression of multiple antigens, which is impossible when staining near-adjacent sections. Our experience has shown SIMPLE to be a useful tool for up to six repeated reprobes. Beyond this, some physical tissue degradation becomes apparent and image quality is reduced. We believe that this degradation may be associated with either the physical handling of slides or the repeated dehydration of tissue in ethanol, as extended exposure to the acidic permanganate solution itself (up to 30 minutes) caused no obvious deleterious effects on tissue quality (data not shown). Thus, development of gentler slide-handling methods should allow increased numbers of probes to be applied.

SIMPLE has multiple applications. For example, simultaneous visualization of different phosphorylation sites as well as total protein expression within specific cell types could reveal important information about signaling pathway activation status in normal and neoplastic tissues. The method should be easily adapted for in situ hybridization. SIMPLE can be easily performed by any lab already conducting traditional immunohistochemistry methods on paraffin sections, and it should find a number of practical uses in both research and diagnostic laboratories.

BIBLIOGRAPHY

1. Niki T et al. (2002) Frequent co-localization of Cox-2 and laminin-5 gamma2 chain at the invasive front of early-stage lung adenocarcinomas. Am J Pathol 160:1129-1141
2. Camp R L, Chung G G, Rimm, D L (2002) Automated subcellular localization and quantification of protein expression in tissue microarrays. Nat Med 8:1323-1327
3. Robertson D, et al. (2008) Multiple immunofluorescence labelling of formalin-fixed paraffin-embedded (FFPE) tissue. BMC Cell Biol 9:13
4. Dandrea M R, et al. (2001) Application of triple immunohistochemistry to characterize amyloid plaque-associated inflammation in brains with Alzheimer's disease. Biotech Histochem 76:97-106
5. Furuya T. et al. (2004) A novel technology allowing immunohistochemical staining of a tissue section with 50 different antibodies in a single experiment. J Histochem Cytochem 52:205-210
6. Tramu G, Pillez A, Leonardelli J (1978) An efficient method of antibody elution for the successive or simultaneous localization of two antigens by immunocytochemistry. J Histochem Cytochem 26: 322-324
7. Wang B L, Larsson L I (1985) Simultaneous demonstration of multiple antigens by indirect immunofluorescence or immunogold staining. Novel light and electron microscopical double and triple staining method employing primary antibodies from the same species. Histochemistry 83:47-56
8. Schubert W. et al. (2006) Analyzing proteome topology and function by automated multidimensional fluorescence microscopy. Nat Biotechnol 24:1270-1278
9. Pirici et al., (2009) Antibody elution method for multiple immunochemistry on primary antibodies raised in the same species and of the same subtype. J. Histochem. Cytochem. 57(6):567-575 (epublished Feb. 16, 2009)
10. Caruccio et al., 2002, Vox Sanguinis, 83:63-96

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for detecting at least two antigens in a cell or tissue sample, said method comprising:
   a. obtaining a cell or tissue sample;
   b. processing said cell or tissue sample for antigen detection wherein said detection is on a slide;
   c. labeling and detecting at least one antigen in said cell or tissue sample and capturing an image of said at least one antigen, and optionally simultaneously detecting at least two labeled antigens, wherein said labeling is selected from the group consisting of immunohistochemical, immunogold, and in situ labeling;
   d. erasing said label from said cell or tissue sample, wherein said label comprises a chromogenic substrate and said substrate is soluble in an organic alcohol solvent;
   e. processing said cell or tissue sample to retrieve said at least one antigen using microwave antigen retrieval;
   f. reprobing said cell or tissue sample by labeling and detecting at least one different antigen in said cell or tissue sample and capturing an image of said at least one different antigen;
   g. optionally determining the level of at least one antigen of step c and optionally determining the level of at least one antigen of step f;
   h. optionally counterstaining said cell or tissue before or after detection of said antigens; and
   i. scanning said slide using a whole slide digital scanning microscope after said cell or tissue sample is stained or labeled, capturing a digital image of said stained or labeled cell or tissue sample, importing said digital image into a program for processing images, and optionally visualizing said image;

thereby detecting at least two antigens in a cell or tissue sample.

2. The method of claim 1, wherein said cell or tissue is human.
3. The method of claim 1, wherein at least one of said at least two antigens is a protein.
4. The method of claim 3, wherein all antigens are proteins.
5. The method of claim 3, wherein said protein is selected from the group consisting of Glial Fibrillary Acidic Protein (GFAP), S100-beta, MAP2, Calbindin, Neurofilament protein, Synaptophysin, Adrenocorticotropic Hormone, Thyroid Stimulating Hormone, Luteinizing Hormone, and Human Chorionic Gonadotropin (alpha-subunit).
6. The method of claim 1, wherein said label is erased by dissociating an antibody-label complex from the antigen.
7. The method of claim 1, wherein said processed cell or tissue has been affixed to a substrate.
8. The method of claim 7, wherein said substrate is selected from the group consisting of a slide, a tissue culture chamber slide, a coverslip, a tissue culture dish, and a multiwell plate.
9. The method of claim 7, wherein at least two antigens are detected simultaneously.
10. The method of claim 7, wherein at least two antigens are visualized simultaneously.
11. The method of claim 1, wherein images are captured for said at least two detected antigens.
12. The method of claim 11, wherein said images are captured separately after consecutive detection of said at least two antigens and said images are processed for simultaneous visualization of two or more images captured from said cell or tissue sample.
13. The method of claim 1, wherein at least two antigens are detected in the same cell.
14. The method of claim 1, wherein said immunohistochemical labeling comprises the use of an enzyme-coupled antibody.
15. The method of claim 14, wherein said enzyme is a peroxidase or an alkaline phosphatase.
16. The method of claim 14, wherein said substrate is selected from the group consisting of 3-amino-9-ethylcarbazole, 3,3',5,5'-Tetramethylbenzidine, 4-chloro-11-naphthol, Fast Blue BB, NBT/BCIP, Fast Red, and AP-Fast Red.
17. The method of claim 14, wherein when said substrate is precipitated, said precipitated substrate is non-permanent.
18. The method of claim 1, wherein at least five antigens are detected.
19. The method of claim 18, wherein six antigens are detected.
20. The method of claim 1, wherein said cell or tissue sample is counterstained.

21. The method of claim 20, wherein said counterstain is selected from the group consisting of hematoxylin, nuclear fast red, methyl green, and methylene blue.

22. The method of claim 1, wherein said erasing comprises destaining and antibody stripping.

23. The method of claim 22, wherein acidified permanganate is used for said antibody stripping.

24. The method of claim 1, wherein said at least one antigen is detected in a cell or tissue sample affixed to a slide.

25. The method of claim 24, wherein at least two cells or tissue samples are affixed to said slide.

26. The method of claim 1, wherein said image is visualized.

27. The method of claim 26, wherein said images are processed and overlaid for simultaneous visualization.

28. The method of claim 26, wherein said program is adjusted to create false-color composites.

29. The method of claim 26, wherein images of at least two detected antigens are captured.

30. The method of claim 26, wherein at least two images captured from a cell or tissue sample are overlaid to form a composite image and said composite image is visualized.

31. The method of claim 1, wherein said method comprises sequential immunoperoxidase labeling and erasing.

32. The method of claim 1, wherein said processing of said cell or tissue sample is selected from the group consisting of fixation and paraffin-embedding, freezing, cytologic smears, cytospin preparations, and aspirates.

33. The method of claim 26, wherein said method is automated.

34. The method of claim 1, wherein at least two cells or tissue samples are processed simultaneously.

35. A method for diagnosing a disease or disorder associated with a change in the level or expression of at least two antigens, said method comprising obtaining a sample from a test subject, comparing the level of said at least two antigens in said test subject with the level of said at least two antigens from an otherwise identical sample from an unaffected subject or from an otherwise identical unaffected sample from said test subject using the method of claim 1, wherein a higher or lower level of said at least two antigens in said sample from a test subject, compared with the levels of said at least two antigens in said sample from an unaffected subject or from an unaffected sample from said test subject, is an indication that said test subject has said disease or disorder associated with said at least two antigens.

36. The method of claim 35, wherein at least five antigens are compared.

* * * * *